(12) United States Patent
Horak et al.

(10) Patent No.: US 8,158,165 B2
(45) Date of Patent: Apr. 17, 2012

(54) PREVENTATIVE TREATMENT AND REMISSION OF ALLERGIC DISEASES

(75) Inventors: Roelof Marthinus Horak, Pretoria (ZA); Ebrahim Wadiwala, Pretoria (ZA); Gerda Fouche, Pretoria (ZA); Marina Mikhailovna Van Der Merwe, Pretoria (ZA); Vinesh Jaichand Maharaj, Centurion (ZA); Louis Gabriel Jozua Ackerman, Pretoria (ZA)

(73) Assignee: CSIR (ZA)

( * ) Notice: Subject to any disclaimer, the term of this patent is extended or adjusted under 35 U.S.C. 154(b) by 179 days.

(21) Appl. No.: 12/718,190

(22) Filed: Mar. 5, 2010

(65) Prior Publication Data

US 2010/0168227 A1    Jul. 1, 2010

Related U.S. Application Data

(62) Division of application No. 12/281,517, filed as application No. PCT/IB2007/050649 on Feb. 28, 2007, now abandoned.

(30) Foreign Application Priority Data

Mar. 3, 2006  (ZA) ....................... 06/1860

(51) Int. Cl.
    *A01N 65/00*    (2009.01)
(52) U.S. Cl. ...................................... 424/725
(58) Field of Classification Search .................. None
    See application file for complete search history.

(56) References Cited

FOREIGN PATENT DOCUMENTS

| JP | 09124677 | 5/1997 |
|---|---|---|
| JP | 09143086 | 6/1997 |
| JP | 2001187725 | 7/2001 |
| JP | 2001192338 | 7/2001 |
| JP | 2001261545 | 9/2001 |
| JP | 2003111581 | 4/2003 |
| JP | 2004269450 | 9/2004 |
| JP | 2004323362 | 11/2004 |
| JP | 2004323466 | 11/2004 |
| WO | WO 9953935 | 10/1999 |
| WO | WO 0130367 | 5/2001 |

OTHER PUBLICATIONS

Taylor et al: "Investigating the safety of plants used in South African traditional medicine: Testing for genotoxicity in the micronucleus and alkaline comet assays." Environmental and Molecular Mutagenesis; Vo. 42, No. 3, 2003; pp. 144-154.

Steenkamp et al: "Antioxidant and genotoxic properties of South African herbal extracts." Mutation Research, Genetic Toxicology and Environmental Mutagenesis, Elsevier, Amsterdam, NL; vol. 581, No. 1-2, Mar. 7, 2005; pp. 35-42.

Holzapfel et al: "Furanoterpenoids from *Siphonochilus aethiopicus*" Phytochemistry, Pergramon Press, GB; vol. 59, No. 4, Feb. 2002; pp. 405-407.

Viljoen et al: "The essential oil composition of the roots and rhizomes of *Siphonochilus aethiopicus*." South African Journal of Botany— Suid-Afrikaans Tydskrift Vir Plantkunde, Foundation for Education, Science and Technology, Pretoria, SA; vol. 68, No. 1, 2002; pp. 115-116.

Viljoen et al., South African Journal of Botany, pp. 115-116, 68, 2002.

International Search Report and Written Opinion prepared by the European Patent Office on Nov. 14, 2007 for International Application No. PCT/IB2007/050649; Applicant, CSIR.

International Preliminary Report on Patentability prepared by the European Patent Office on May 23, 2008 for International Application No. PCT/IB2007/050649; Applicant, CSIR.

*Primary Examiner* — Michael Meller
(74) *Attorney, Agent, or Firm* — Sheridan Ross P.C.

(57) ABSTRACT

The invention provides the use of at least one plant selected from plants of the family Zingiberaceae in the preparation of a medicament for use in the treatment or prophylaxis of allergic diseases. The plant is optionally selected from the genera *Siphonochilus*, *Kaempferia*, *Cienkowskia* and *Cienkowskiella* and the species is optionally selected from *Siphonochilus aethiopicus*, *Siphonochilus natalensis*, *Kaempferia aethiopica*, *Kaempferia natalensis*, *Kaempferia ethelae*, *Cienkowskia aethiopica* and *Cienkowskiella aethiopica*. The allergic disease is selected from asthma and atopy.

6 Claims, 5 Drawing Sheets

PREVENTATIVE TREATMENT AND REMISSION OF ALLERGIC DISEASES

CROSS REFERENCE TO RELATED APPLICATION

This application is a divisional of U.S. patent application Ser. No. 12/281,517 filed on Sep. 3, 2008, which is a 371 of PCT/IB2007/050649 filed Feb. 28, 2007, which claims the benefit of South African Application No. 2006/01860 filed Mar. 3, 2006. The entire disclosure of the prior application is considered to be part of the disclosure of the accompanying application and is hereby incorporated by reference.

FIELD OF THE INVENTION

THIS INVENTION relates to compounds useful in the preventative treatment and remission of allergic diseases. More specifically, this invention relates to compounds useful in the preventative treatment and remission of asthma and/or atopy.

BACKGROUND AND SUMMARY OF INVENTION

Glucocorticoids are widely used in the preventative treatment of asthma and other allergic diseases. Glucocorticoids bind to the glucocorticoid receptor (GR), thereby activating the GR. The activated GR then binds to a glucocorticoid responsive element and upregulates the genes for anti-inflammatory agents such as lipocortin. The induction of the anti-inflammatory protein lipocortin in turn inhibits the enzyme phospholipase A2, thereby decreasing the production of allergy mediators, such as prostaglandins and leukotrienes. *Allergy and Allergic Diseases: The new Mechanism and Therapeutics*, edited by J. A. Denburg, *Human Press Inc.*, Totowa, N.J., Schleimer R P, *Effects of Glucocorticosteroids on inflammatory cells relevant to their Therapeutic Application in Asthma, Am. Rev. Respir. Dis.*, 1990, 141, S59-S69.

One of the other main effects of activated GR is the down-regulation of a wide variety of agents, including cytokines and chemokine agents such as Interleukin-4 (IL-4) and Interleukin-5 (IL-5). The ability of glucocorticoids to inhibit the production of cytokines, in particular IL-5, has proven to be a major component in their effectiveness in the treatment of allergic diseases and, especially, asthma and atopy.

Furthermore, phosphodiesterase isoenzymes (PDE's), and more particularly inhibitors of PDE 4, are receiving special interest as anti-asthmatic agents due to evidence that these enzymes can act as both anti-inflammatory agents and bronchodilators in both animals and humans. Cortijo J, Beleta J, Cardelus I, Llenas E, Morcillo E., *Investigation into the role of phosphodiesterase IV in bronchorelaxation, including studies with human bronchus, Br. J. Pharmcol.*, 1993, 108, 562-568.

Leukotrienes are also of particular interest in the study of allergic disease, because of their marked bronchoconstrictory action. Leukotrienes have an approximate 1000-fold greater bronchoconstrictory action than histamines and prostaglandins. Leukotrienes are by-products of arachidonic acid which is located in phospholipid bi-layers in the cell membranes of mast cells. During an asthma attack, arachidonic acid is converted into five leukotrienes. This conversion is mediated by an enzyme, 5-lipoxygenase (5-LO), which converts arachidonic acid first to 5-hydroxyperoxyeicosatetraenoic acid (5-HPETE) and then into leukotriene A4 (LTA4), which is the precursor of the other four leukotrienes. Of the five leukotrienes produced during an asthma attack, the cysteinyl class of leukotrienes (LTC4, LTD4 and LTE4) are the most potent bronchoconstrictors. Werz O, Steinhilber D, *Therapeutic options for 5-lipoxygenase inhibitors, Pharmacology and Therapeutics*, 2006, 112, 701-718.

Within this process, leukotriene biosynthesis inhibitors have an important role to play, since they inhibit the action of 5-LO, thereby inhibiting the eventual synthesis of the bronchoconstrictory leukotrienes.

The above pathway may thus be manipulated by administering a glucocorticoid receptor (GR) binding compound, a PDE inhibitor and/or a 5-LO inhibitor to a patient in need thereof. Currently, this is accomplished in most cases by administering steroidal compounds to a patient suffering from an allergic disease or reaction, such as asthma or atopy. Due to many detrimental side-effects being associated with steroidal compounds in treating such diseases, there is a need for a non-steroidal compound exhibiting the beneficial properties associated with steroidal compounds and steroid-containing formulations.

In chronic inflammatory diseases, such as asthma, rheumatoid arthritis, inflammatory bowel disease and psoriasis, several cytokines recruit activated immune and inflammatory cells to the site of lesions, thereby amplifying and perpetuating the inflammatory state. These activated cells produce many other mediators of inflammation. The vicious cycle may be suppressed by glucocorticoid or immunosuppressive therapy, but there is no curative treatment for any chronic inflammatory disease. Transcription factors play a key role in immune and inflammatory responses and one ubiquitous transcription factor of particular importance is nuclear factor-κB (NF-κB). NF-κB is a central mediator of the human immune response, regulating the transcription of various pro-inflammatory and inflammatory mediators such as the cytokines Interleukin-1 (IL-1), Interleukin-2 (IL-2), Interleukin-8 (IL-8) and TNF-α, as well as genes encoding cyclo-oxygenase II, nitic oxide synthase, immunoreceptors, cell adhesion molecules, or acute phase proteins. In clinical studies of patients with allergic asthma, plasma levels of Interleukin-8 (IL-8) were elevated in these patients. Blackwell T S, Christian J W, *The role of nuclear factor-κB in cytokine gene regulation. Am. J. Respir. Cell Mol Biol* 1997; 17:3-9, Hashimoto, S., Matsumoto, K., Gon, Y. et al. 2000. p 38 *MAP kinase regulates TNF alpha-, IL-1 alpha-and PAF-induced RANTES and GM-CSF production by human bronchial epithelial cells. Clinical and Experimental Allergy.* 30: 48-55. Herlaar, E. and Brown, Z. 1999. p 38 *MAPK signaling cascades in inflammatory disease. Molecular Medicine Today.* 5: 439-447. Holden, N. S., Catley, M. C., Cambridge, L. M., Barnes, P. J. and Newton, R. 2004. *ICAM-1 expression is highly NF-kappaB-dependent in A549 cells. European Journal of Biochemistry.* 271: 785-791. Therefore, inhibition of NF-κB resulting in the down regulation of chemokines such as IL-8 could be beneficial in the treatment of asthma and inflammatory diseases.

According to one aspect of the invention, there is provided an organic solvent extract or an essential oil of a plant of the family Zingiberaceae for use in the preventative treatment and remission of allergic diseases.

The plants of the family Zingiberaceae include the genera *Siphonochilus, Kaempferia, Cienkowskia* and/or *Cienkowskiella*.

The organic solvent extract or essential oil may be obtained from plant material of plants selected from the species *Siphonochilus aethiopicus, Siphonochilus natalensis,*

*Kaempferia aethiopica, Kaempferia natalensis, Kaempferia ethelae, Cienkowskia aethiopica* and *Cienkowskiella aethiopica*.

Preferably, the said organic solvent extract or essential oil comprises as an active ingredient a compound having the structural formula 1:

(1)

(4a-S, 5R, 8a-R or 4a-R, 5S, 8a-S)

The chemical name (IUPAC) of the compound of formula 1 is 4,4a,5,9-tetrahydro-3,5,8a-trimethylnaptho[2,3-b]furan-8-one.

The compound of formula 1 may be used in the form of a racemic mixture or in the form of one of its steroisomers.

Examples of the allergic diseases are asthma and atopy.

Typically, the organic solvent extract or essential oil is capable of binding to a glucocorticoid receptor (GR), inducing the production of lipocortin, and/or the inhibition of the enzyme phospholipase A2, and/or the decreasing of production of prostaglandins and/or leukotrienes.

The organic solvent extract or essential oil may have anti-bronchoconstrictory activity and further may downregulate cytokines and chemokine agents such as Interleukin-4 (IL-4) and Interleukin-5 (IL-5).

The organic solvent extract or essential oil may inhibit NF-κB a central mediator of the human immune response, down regulating the transcription of various pro-inflammatory and inflammatory mediators such as the cytokines Interleukin-8 (IL-8)

The organic solvent extract or essential oil may be obtainable by a method which includes the steps of preparing an extract from plant material of a plant of the family Zingiberaceae, and separating a fraction having activity against allergic diseases, the extracts containing the active ingredient having activity against allergic diseases.

The method may include the steps of extracting wet rhizomes or roots or ground plant samples of said plant species such as *Siphonochilus aethiopicus*, or drying the rhizomes and/or the roots of the plant by air drying or oven drying, followed by grinding of the rhizomes and/or roots to a powder. Extracts are prepared by extraction using organic solvents such as diethyl ether, di-isopropyl ether, t-butyl methyl ether, t-butyl ethyl ether, ethyl acetate or benzyl acetate. The active ingredient may be extracted by extraction techniques which include steam distillation, and or purification of the extracts using solvent/solvent partitioning and/or chromatographic separating techniques.

According to another aspect of the invention, there is provided a substance or composition for use in a method for the preventative treatment and remission of allergic diseases, which substance or composition includes as an active ingredient an extract as described above, and said method comprising administering to a subject an effective dosage of said substance or composition.

According to another aspect of the invention, there is provided a substance or composition for use in a method for the preventative treatment and remission of allergic diseases, which substance or composition includes as an active ingredient a compound of formula 1, and said method comprising administering to a subject an effective dosage of said substance or composition.

According to a further aspect of the invention, there is provided a compound of formula 1 for use in a method for the preventative treatment and remission of allergic diseases.

According to another aspect of the invention, there is provided the use of the organic solvent extract or essential oil as described above in the manufacture of a medicament having activity against allergic diseases.

Examples of the allergic diseases are asthma and atopy.

According to still a further aspect of the invention, there is provided a composition for use in the preventative treatment and remission of allergic diseases, which includes an effective quantity of one of said extract, said compound of formula 1 or said essential oil.

The extract, and compositions of the extract, may be in a form suitable for administering to mammalian subjects, particularly human subjects. The extract may be in the form of an organic solvent extract and/or an essential oil or combinations thereof.

The invention extends to the use of the organic solvent extract as described above, the essential oil or the compound of formula 1 in the downregulation of glucocorticoid receptors, the inhibition of phospholipase A2, the downregulation of allergy mediators such as prostaglandins and leukotrienes, the downregulation of cytokines such as IL-4 and IL-5, the inhibition of phosphodiesterase 4, the inhibition of 5-lipoxygenase or leukotriene biosynthesis, and the inhibition of specific activity of the NF-κB Transcription Response resulting in down regulation of IL-8.

More particularly, the invention provides the use of an extract of at least one plant selected from plants of the family Zingiberaceae in the preparation of a medicament for use in the treatment or prophylaxis of allergic diseases.

The at least one plant may be selected from the genera *Siphonochilus*, *Kaempferia*, *Cienkowskia* and *Cienkowskiella* and from the species *Siphonochilus aethiopicus*, *Siphonochilus natalensis*, *Kaempferia aethiopica*, *Kaempferia natalensis*, *Kaempferia ethelae*, *Cienkowskia aethiopica* and *Cienkowskiella aethiopica*.

The extract may include, as an active ingredient, a compound selected from compounds having the structural formula 1, (1)

(4a-S, 5R, 8a-R or 4a-R, 5S, 8a-S)

stereoisomers thereof and mixtures of stereoisomers thereof.

The allergic disease may be selected from asthma and atopy.

The extract may be an essential oil obtained by steam distillation of plant material from the at least one plant. Instead, the extract may be an organic solvent extract obtained by extraction of plant material of the at least one plant with an organic solvent.

The organic solvent may be an ether selected from diethyl ether, diisopropyl ether, t-butyl methyl ether, t-amyl methyl ether and t-butyl ethyl ether. Instead, the organic solvent may be an ester selected from methyl acetate, ethyl acetate and benzyl acetate.

The plant material may be obtained from roots or rhizomes of the plant.

The invention extends to a composition for use in a method of treatment or prophylaxis of allergic diseases, the composition including an extract of at least one plant selected from plants of the family Zingiberaceae.

The at least one plant may be as hereinbefore described.

The extract may be as hereinbefore described.

The allergic disease may be selected from asthma and atopy and the plant material may be obtained from roots or rhizomes of the plant.

The invention extends to the use of an extract of at least one plant selected from plants of the family Zingiberaceae in the preparation of a medicament for use in any one or more of the downregulation of glucocorticoid receptors, the inhibition of phospholipase A2, the downregulation of allergy mediators, the downregulation of cytokines, the inhibition of phosphodiesterase 4, the inhibition of 5-lipoxygenase or leukotriene biosynthesis, and the inhibition of specific activity of the NF-κB Transcription Response.

The allergy mediators may be selected from prostaglandins and leukotrienes. The cytokines may be selected from IL-4, IL-5 and IL-8.

The at least one plant may be as hereinbefore described.

The extract may be as hereinbefore described.

The allergic disease may be selected from asthma and atopy.

The plant material may be obtained from roots or rhizomes of the plant.

The invention extends, further, to the use of a compound selected from compounds having the structural formula 1, (1)

(4a-S, 5R, 8a-R or 4a-R, 5S, 8a-S)

stereoisomers thereof and mixtures of stereoisomers thereof in the preparation of a medicament for use in the treatment or prophylaxis of allergic diseases.

The allergic disease may be selected from asthma and atopy.

The invention extends further to a method of treatment of an allergic disease, the method including administering to a person or animal in need of treatment a therapeutically effective amount of an extract, a composition or a compound selected from compounds of structural formula 1 as hereinbefore described.

The allergic disease may be as hereinbefore described.

The invention will now be described, by way of example, with reference to the accompanying diagrammatic drawings and tables.

DETAILED DESCRIPTION OF PARTICULAR EMBODIMENTS

The plant extract or distillate of the invention may be produced by extraction from wet rhizomes, roots or ground plant samples of *Siphonochilus aethiopicus*, or drying the rhizomes and/or the roots of the plant by air drying or oven drying, followed by grinding of the rhizomes and/or roots to a powder. The active ingredient thereof may be extracted by extraction techniques which include steam distillation and solvent extraction. The compound may be refined further by separating individual compounds from the extract or distillate using solvent/solvent partitioning and/or chromatographic separating techniques. These techniques are discussed in more detail in the illustrative Examples below.

Example 1

Aqueous Infusion and Fractionation of Plant Material

Figure 1:
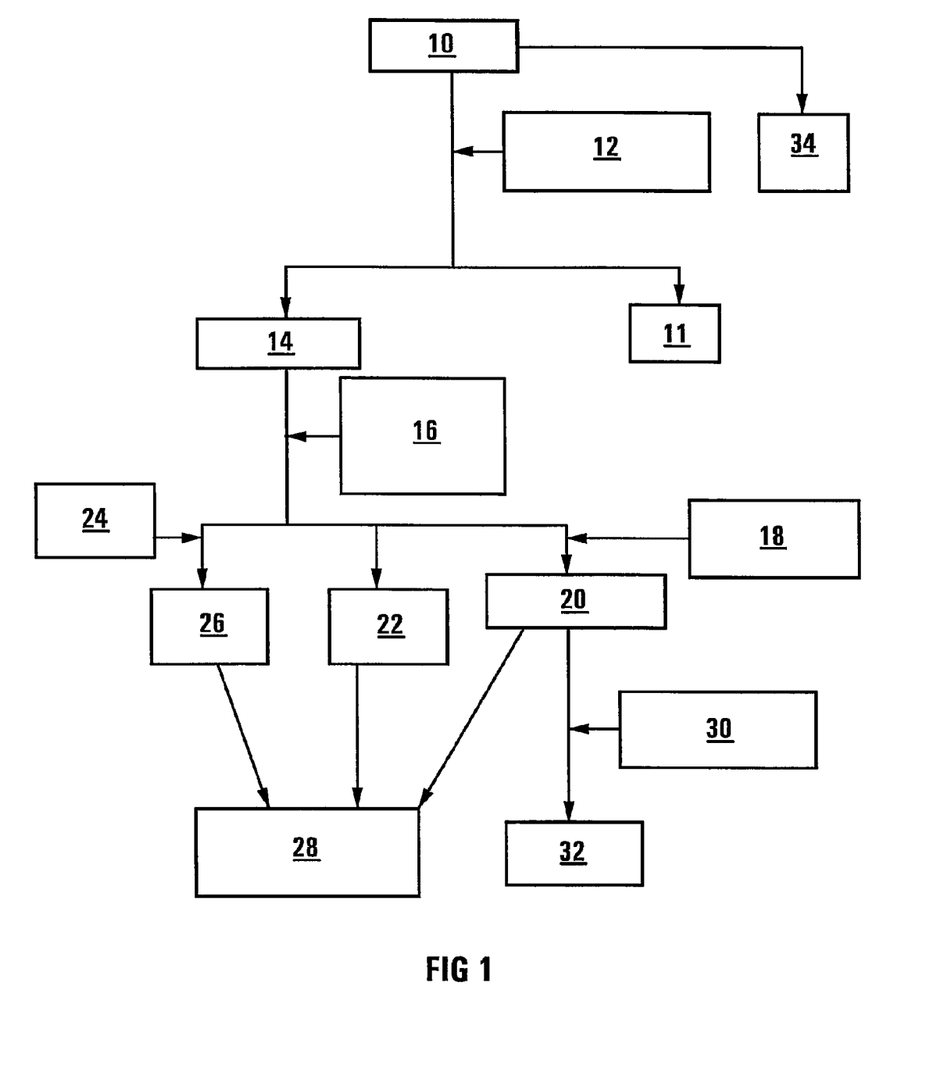
FIG. 1 shows a flow diagram illustrating a protocol for the extraction of the compound of formula 1.

As shown in FIG. 1, an infusion 14 is prepared from plant material such as leaves, rhizomes or roots. One litre of deionised boiling water, shown at 12, is added to 22.08 g of oven dried (60° C.) ground rhizomes, shown at 10, and left to stand for 1 hour with occasional stirring. The water is filtered and solids 11 are removed and the aqueous phase is extracted four times with 500 ml of diethyl ether, as shown at 16. The extracts obtained from each extraction are combined, dried, filtered and the solvent removed by means of a rotary evaporator in a water bath at a temperature of 25° C., as shown at 18, to produce an ether portion 20 (WG13A) weighing 119 mg, which is designated the organic fraction. An intermediate layer in the form of a solid 22 (WG13D) forms during the liquid-liquid partitioning. Approximately 107 mg of solid 22 is obtained, which is kept separate. The aqueous layer is freeze-dried, as shown at 24, to yield 2.52 g of solid material 26 (WG13B) which is designated the aqueous fraction. The compound of formula 1 is present in the organic fraction and is identified using thin layer chromatography. The compound may then be purified further using column chromatography.

Example 2

Organic Extraction of Plant Material

Instead of following the method of Example 1, and again with reference to FIG. 1, one litre of diethyl ether is added to 22.08 g of oven dried (60° C.) ground rhizomes and left to stand for 1 hour with occasional stirring. The ether is filtered and carefully evaporated under low vacuum to yield a dry extract 34 (WG-I-101 or WG-I-58A) of approximately 1.5 g. The compound of formula 1 is identified in the organic extract by using thin layer chromatography.

Example 3

Fractionation of Organic Extract

The diethyl ether extracts produced by either the aqueous extraction or the organic extraction procedures described above was purified further by flash chromatography (silica gel), as shown at 30, using ethyl acetate-hexane (1:9, v/v) as eluent to yield the sesquiterpenoid of formula 1 WG13C or WG-I-94B, as shown at 32.

An essential oil is obtained by steam distillation of the rhizomes and/or roots of the plant species *Siphonochilus aethiopicus*. The chemical compositions of the major components of the essential oil are shown in Table 1 below. Identification of the major components is accomplished by using combined gas chromatography-mass spectrometry and the Kovats Indices technique. The sesquiterpenoid of formula 1 crystallizes at the interface of the essential oil and the condensate obtained during the steam distillation process. Upon subsequent cooling of the essential oil to below 4° C., the compound of formula 1 crystallizes from the oil.

TABLE 1

Essential oil chemical composition (refer to Table 20 for the IUPAC nomenclature of the compounds listed in Table 1)

| Retention time (min) | Retention Index | Compound | Compounds as a % in oil |
|---|---|---|---|
| 7.45 | 940 | Alpha-pinene | 1.02 |
| 8.52 | 976 | Sabinene | 4.96 |
| 8.98 | 992 | Myrcene | 1.61 |
| 9.57 | 1011 | Delta-3-carene | 1.47 |
| 9.97 | 1025 | Alpha-terpinene | 0.85 |
| 10.12 | 1030 | Beta-phellandrene | 7.13 |
| 10.34 | 1037 | Cis-ocimene | 1.86 |
| 10.66 | 1048 | Trans-beta-ocimene | 10.83 |
| 11.00 | 1059 | Gamma-terpinene | 1.08 |
| 13.10 | 1129 | Allo-neo-ocimene | 8.90 |
| 13.48 | 1142 | Allo-ocimene | 16.00 |
| 20.85 | 1400 | Beta-elemene | 1.23 |
| 23.28 | 1489 | Germacrene-D | 1.39 |
| 24.52 | 1537 | Kessane | 13.25 |
| 25.27 | 1567 | Germacrene-B | 9.81 |
| 32.10 | 1856 | Compound of Formula | 9.32 |

Example 4

Steam Distillation

Approximately 600 g of fresh rhizomes and/or roots are washed with water and air dried. The fleshy roots are separated from the rhizomes. The roots are crushed and the rhizomes are sliced into slices having a thickness of approximately 2-3 mm each. Both the roots and the sliced rhizomes are steam-distilled in a steam distillation unit for 3 h. One litre of condensate is collected in a separating funnel. The crystals which form in the condenser are washed out with deionised water and filtered though a sintered glass funnel. The crystals contain the compound of formula 1.

The mixture of the essential oil and water in the separating funnel condensate is allowed to stand at room temperature for 16 h. The resulting crystals present on the surface, comprising the compound of formula 1, are removed by draining of the condensate and filtering using a sintered glass funnel. A total of 480 mg of the compound of formula 1 is thus obtained.

The structural assignment of the compound of formula 1 is based on a detailed study of the high field $^1$H and $^{13}$C nuclear magnetic resonance (NMR) spectral data of the compound. The first stage in the characterisation of the compound is the identification of the $^1$H NMR signals belonging to isolated spin systems. This is achieved by means of two-dimensional (2D) ($^1$H,$^1$H) correlation spectroscopy, using a COSY-45 sequence. The multiplicities of the different resonances in the $^{13}$C NMR spectra are deduced from the coupled $^{13}$C NMR spectra as well from the proton decoupled CH, CH$_2$, and CH$_3$ sub-spectra obtained using a DEPT pulse sequence. The $^{13}$C resonances are partly assigned by correlation of the proton-bearing carbon atoms, with specific resonances in 2D ($^{13}$C, $^1$H) chemical-shift experiments.

Sequence information, as well as the signals of the quaternary carbon atoms, are assigned from the 2-D long-range $^{13}$C—{$^1$H} chemical shift experiments (HMBC), as shown in Tables 2, 3 and 4 below:

TABLE 2

$^1$H (500 MHz) NMR data for the compound of Formula 1 in CD$_2$Cl$_2$

| Hydrogen Atom | J(HH)/Hz | $\delta_H$/p.p.m. |
|---|---|---|
| 2 | — | 7.02 brs |
| 4 axial | 15.9, 11.0, 3.0, 1.7 | 2.16 dddd |
| 4 equit | 15.9, 5.4, 1.7 | 2.74 ddd |
| 4a | 11.0, 10.3, 5.4 | 1.85 ddd |
| 5 | 10.3, 7.2, 2.8, 2.1 | 2.40 dddd |
| 6 | 10.1, 2.1 | 6.72 dd |
| 7 | 10.1, 2.8 | 5.91 dd |
| 9*$_{axial}$ | 16.9, 3.0, 1.7 | 2.64 brd |
| 9*$_{equit}$ | 16.9, 1.7 | 2.71 brd |
| 5-Me | 7.2 | 1.24 d |
| 3-Me | 1.7 | 1.94 d |
| 8a-Me | — | 1.4 s |

*may be interchanged

TABLE 3

$^{13}$C (125.8 MHz) NMR data for the compound of Formula 1 in CD$_2$Cl$_2$

| Carbon Atom | $\delta_C$/p.p.m |
|---|---|
| 2 | 137.83 D |
| 3 | 119.73 S |
| 3a | 115.37 S |
| 4 | 22.89 T |
| 4a | 45.42 D |
| 5 | 34.71 D |
| 6 | 154.82 D |
| 7 | 126.76 D |
| 8 | 204.24 S |
| 8a | 45.32 S |
| 9 | 32.37 T |
| 9a | 149.67 S |
| 5-Me | 18.95 Q |

TABLE 3-continued 13C (125.8 MHz) NMR data for the compound of Formula 1 in $CD_2Cl_2$

| Carbon Atom | $\delta_C$/p.p.m |
|---|---|
| 3-Me | 8.19 Q |
| 8a-Me | 16.95 Q |

Referring to Table 3:

1. Mass spectrum of the compound of Formula 1: m/z 230 ($M^+$); 215 ($M^+$ —$CH_3$); 187 (—CO); 83 (base peak).
2. Optical Rotation $[\alpha]_D$ = +108.8° (c = 1.0, $CH_2Cl_2$)
3. m.p. 89-90° C.

TABLE 4

2D Long-range 13C - {1H} chemical shift experiment (HMBC)

| 13C resonance irradiated | | 1H resonance affected | |
|---|---|---|---|
| Assignment | $\delta_C$/p.p.m | Assignment | $\delta_H$/p.p.m. |
| C-2 | 137.83 | H-3 Me | 1.94 |
| C-3 | 119.73 | H-3 Me | 1.94 |
|  |  | H-4 equit | 2.74 |
| C-3a | 115.37 | H-4 equit | 2.74 |
|  |  | H-4 axial | 2.16 |
|  |  | H-3 Me | 1.94 |
|  |  | H-2 | 7.02 |
| C-4 | 22.89 | H-4a | 1.85 |
| C-4a; C-8a | 45.32, 45.42 | H-6 | 6.72 |
|  |  | H-7 | 5.91 |
|  |  | H-9 | 2.65 |
|  |  | H-5 | 2.40 |
|  |  | H-4 axial | 2.16 |
|  |  | H-4 equit | 2.74 |
|  |  | H-4a | 1.85 |
|  |  | H-5 Me | 1.24 |
|  |  | H-8a Me | 1.04 |
| C-5 | 34.71 | H-6 | 6.72 |
|  |  | H-7 | 5.91 |
|  |  | H-4 axial | 2.16 |
|  |  | H-4a | 1.85 |
|  |  | H-5 Me | 1.24 |
| C-5Me | 18.95 | H-6 | 6.72 |
|  |  | H-5 | 2.40 |
|  |  | H-4a | 1.85 |
| C-6 | 154.82 | H-5 | 2.40 |
|  |  | H-5 Me | 1.24 |
| C-7 | 126.76 | H-5 Me | 1.24 |
| C-8 | 204.24 | H-6 | 6.72 |
|  |  | H-9 | 2.65 |
|  |  | H-4a | 1.85 |
|  |  | H-8a Me | 1.04 |
| C-8aMe | 16.95 | H-9 | 2.65 |
|  |  | H-4a | 1.85 |
| C-9 | 32.37 | H-4a | 1.85 |
|  |  | H-8a Me | 1.04 |
| C-9a | 149.67 | H-9 | 2.65 |
|  |  | H-2 | 7.02 |

The relative stereochemistry of the compound of formula 1, follows from the magnitude of the (1H,1H) coupling constants and the results of the homonuclear 1H-{1H} n.O.e experiments, as shown in Table 5 below:

TABLE 5

(1)

(4a-S,5R,8a-R or 4a-R,5S,8a-S)

Results from homonuclear 1H-{1H} n.O.e. experiments

| Proton transition irradiated | | 1H resonance affected | |
|---|---|---|---|
| Assignment | $\delta_H$/p.p.m. | $\delta_H$/p.p.m. | Assignment |
| 8a-Me | 1.04 | 2.16 | H-4 axial |
|  |  | 2.40 | H-5 |
| H-4 axial | 2.16 | 2.40 | H-5 |
|  |  | 2.74 | H-4 equit |
|  |  | 1.04 | 8a-Me |
| 3-Me | 1.22 | 7.02 | H-2 |
|  |  | 2.74 | H-4 equit |
| 5-Me | 7.18 | 6.72 | H-6 |
|  |  | 2.74 | H-4 equit |
|  |  | 2.40 | H-5 |

Bio-Assays and Inhibition Studies

Biochemical assay results as presented herein are reflected as the percent inhibition of specific binding or activity of a compound. The assay is described in Cidlowski, J. A. and Cidlowski, N. B., *Regulation of glucocorticoid receptors by glucocorticoids in cultured HeLa S3 cells*. Endocrinology 109: 1975-1982, 1981, the contents of which are incorporated herein by way of reference. This assay specifically measures the ability of active glucocorticoids in glucocorticoid receptor downregulation. Responsive test compounds are therefore deemed to possess activities similar to those of active glucocorticoids.

Table 6 (below) shows the results obtained from the screening of a combination of the organic ether fraction (designated WG-I-13A in FIG. 1), the aqueous fraction (designated WG-I-13D in FIG. 1) and the insoluble fraction (designated WG-I-13D in FIG. 1). The combined fraction is designated WG-I-5AB+WG-I-5C, as shown in FIG. 1.

As can be seen from Table 6, significant activity is observed in a glucocorticoid receptor (GR) binding assay (61% inhibition) in HeLa $S_3$ (human epitheloid cervic carcinoma) cells at a concentration of 100 μg/ml of the combined fraction (WG-I-5AB+WG-I-5C) concentration. This assay measures binding of [$^3$H]Dexamethasone to human glucocorticoid receptors. HeLa S3 cells are suspended in modified HEPES buffer, pH 7.2, using standard techniques.

TABLE 6

Bio-assays of combined fractions WG-I-5AB + WG5C (mixture of the insoluble fraction, diethyl ether and aqueous extracts)

| Target | Species | n = | Concentration | Inhibition (%) |
|---|---|---|---|---|
| Phosphodiesterase PDE4 | hum | 2 | 100 μg/ml | 52 |
| Phospholipase $PLA_2$-1 | pig | 2 | 100 μg/ml | 12 |
| Phospholipase $PLA_2$-11 | ca | 2 | 100 μg/ml | −26 |
| Adenosine $A_3$ | rat | 2 | 100 μg/ml | 27 |
| Adrenergic$_2$ | hum | 2 | 100 μg/ml | 25 |
| Glucocorticoid | hum | 2 | 100 μg/ml | 61 |
| Histamine $H_1$, Peripheral | gp | 2 | 100 μg/ml | 40 |

TABLE 6-continued

Bio-assays of combined fractions WG-I-5AB + WG5C (mixture of the insoluble fraction, diethyl ether and aqueous extracts)

| Target | Species | n = | Concentration | Inhibition (%) |
|---|---|---|---|---|
| Interleukin IL-1 | mouse | 2 | 100 µg/ml | 1 |
| Leukotriene $B_4$ | hum | 2 | 100 µg/ml | 20 |
| Leukotriene $D_4$ | gp | 2 | 100 µg/ml | 12 |
| Platelet Activating Factor (PAF) | rabbit | 2 | 100 µg/ml | −1 |
| Prostanoid $EP_1$ | hum | 2 | 100 µg/ml | 33 |
| Prostanoid $EP_4$ | hum | 2 | 100 µg/ml | 35 |

* hum = human; pig = porcine; ca = crotalus atrox; gp = guinea pig; n = number of tubes The cells (1×10$^6$) are incubated with 6 nM [$^3$H]Dexamethasone for 120 minutes at 25° C. Non-specific binding is estimated in the presence of 20 µM Dexamethasone. Membranes are filtered and washed three times and the filters are counted to determine [$^3$H]Dexamethasone specifically bound. Compounds are screened at 10 µM for activity.

Based on the results shown in Table 6, it follows that the combined fraction (WG-I-5AB+WG-I-5C) is effective in binding to the glucocorticoid receptor (GR) site. In addition, significant activity associated with this fraction combination is observed in a phosphodiesterase PDE4 enzyme assay (52% inhibition) in human U937 cells. This inhibitory effect implies that the combined fraction (WG-I-5AB+WG-I-5C) has a bronchodilatory effect. For the PDE4 test, PDE4 which has been partially purified from human U-937 pronocytic cells is used. The test compound and/or vehicle is incubated with 0.2 µg enzyme and 1 µM cAMP containing 0.01 µM [$^3$H]cAMP in Tris buffer pH 7.5 for 20 minutes at 30° C. The reaction is terminated by boiling for 2 minutes and the resulting AMP is converted to adenosine by addition of 10 mg/ml snake venom necleotidase and further incubation at 30° C. for 10 minutes. Unhydrolyzed cAMP is bound to AGI-X2 resin, and remaining [$^3$H]adenosine in the aqueous phase is quantified by scintillation counting. Compounds are screened at 100 µM. IBMX (3-isobutyl-1-methylxanthine) is used as standard reference agent.

Having established the activity specificity of all the fractions combined, the organic ether fraction (WG-I-13A), the aqueous fraction (WG-I-13B), as well as the insoluble fraction which forms at the interface of the organic and extract layer (designated WG-I-13D in FIG. 1), are separately bio-assayed using the glucocorticoid receptor (GR) binding assay and the phosphodiesterase PDE4 enzyme assay described above.

The results obtained from these experiments are shown in Tables 7, 8 and 9 below. An increase in inhibitory activity was observed for the organic ether extract (WG-I-13A) when using the glucocorticoid receptor (GR) binding assay (77% inhibition), as well as the phosphodiesterase PDE4 enzyme inhibition assay (57% inhibition), at an extract concentration of 100 µg/ml. No significant activity was observed for either the aqueous fraction (WG-I-13B) or the insoluble interface fraction (WG13D).

TABLE 7

Inhibition bio-assays for WG13B (aqueous extract)

| Target | Species | n = | Concentration | Inhibition (%) |
|---|---|---|---|---|
| Phosphodiesterase PDE4 | hum | 2 | 100 µg/ml | 15 |
| Glucocorticoid | hum | 2 | 100 µg/ml | 11 | hum = human; n = number of tubes

TABLE 8

Inhibition bio-assays for WG-I-13A (diethyl ether extract)

| Target | Species | n = | Concentration | Inhibition (%) |
|---|---|---|---|---|
| Phosphodiesterase PDE4 | hum | 2 | 100 µg/ml | 57 |
| Glucocorticoid | hum | 2 | 100 µg/ml | 77 | hum = human; n = number of tubes

TABLE 9

Inhibition bio-assays for WG-I-13D (insoluble fraction)

| Target | Species | n = | Concentration | Inhibition (%) |
|---|---|---|---|---|
| Phosphodiesterase PDE4 | hum | 2 | 100 µg/ml | −9 |
| Glucocorticoid | hum | 2 | 100 µg/ml | 5 | hum = human; n = number of tubes

Chemical fingerprinting of the organic fraction 20 (WG-I-13A) using LC-MS (combined liquid chromatography-mass spectroscopy) did not indicate the presence of steroidal-type compounds. Fractionation of the organic fraction led to the isolation of a major compound which was chemically characterised and identified as the sesquiterpenoid compound of formula 1 (designated WG-I-13C in FIG. 1). The sesquiterpenoid compound was screened for activity, once again using the glucocorticoid receptor (GR) binding assay and the phosphodiesterase PDE4 enzyme assay described above. The results of these experiments are shown in Table 10 below.

TABLE 10

Inhibition bio-assays for WG-I-13C (compound 1)

| Target | Species | n = | Concentration | Inhibition (%) |
|---|---|---|---|---|
| Phosphodiesterase PDE4 | hum | 2 | 100 µg/ml | 35 |
| Glucocorticoid | hum | 2 | 100 µg/ml | 104 | hum = human; n = number of tubes

A lower, non-significant activity was observed for the phosphodiesterase PDE4 enzyme assay (35% inhibition) while 104% activity was observed for the glucocorticoid receptor (GR) binding assay at 100 µg/ml of the pure compound concentration. This implies that the sesquiterpenoid compound per se does not have the most significant role to play in bronchodilation, and, in the plant extract of the invention, other compounds present contribute towards the bronchodilatory effect.

The $IC_{50}$ value of the sesquiterpenoid compound in the glucocorticoid-binding assay was determined as being 50.3 µM, as shown in Table 11 below.

TABLE 11

Determination of $IC_{50}$ value of sesquiterpenoid compound (1)

| Primary Biochemical Assay | Species | Conc. | Inhibition (%) | $IC_{50}$ | $K_i$ | $n_H$ |
|---|---|---|---|---|---|---|
| Glucocorticoid | hum | 100 µM | 70 | 50.3 µM | 22.8 µM | 1.4 | hum = human; conc. = concentration

In addition, significant activity was observed for the sesquiterpenoid compound in a 5-lipoxygenase enzyme assay (5-LO), namely 99% inhibition at 100 µg/ml of the pure compound concentration. The results of this experiment are shown in Table 12 below. For the 5-LO test a crude 5-lipoxygenase enzyme preparation from rat basophilic leukemia cells (RBL-1) is used. The test compound is pre-incubated with the enzyme for 5 minutes in Tris buffer pH 7.2 at room temperature. The reaction is initiated by addition of 15 µM arachidonic acid as substrate and run for an additional 8 minutes after which the reaction is terminated by addition of 70 mM citric acid and levels of 5-HETE are determined by radioimmune assay. Compounds are screened at 30 µM. NDGA (nordihydroguaretic acid) is used as standard reference agent.

TABLE 12

Sesquiterpenoid 5-lipoxygenase and phosphodiestrase PDE4 inhibition bio-assays

| Compound code | Species | n = | Concentration | Inhibition (%) |
|---|---|---|---|---|
| Lipoxygenase 5-LO | | | | |
| CIR-55 Essential Oil | hum | 2 | 100 µg/ml | 99 |
| CIR-63 Ether Extract | hum | 2 | 100 µg/ml | 101 |
| CIR-65 Sesquiterpenoid | hum | 2 | 100 µg/ml | 99 |
| Phosphodiesterase PDE4 | | | | |
| CIR-55 Essential Oil | hum | 2 | 100 µg/ml | 73 | hum = human; n = number of tubes

Figure 6:
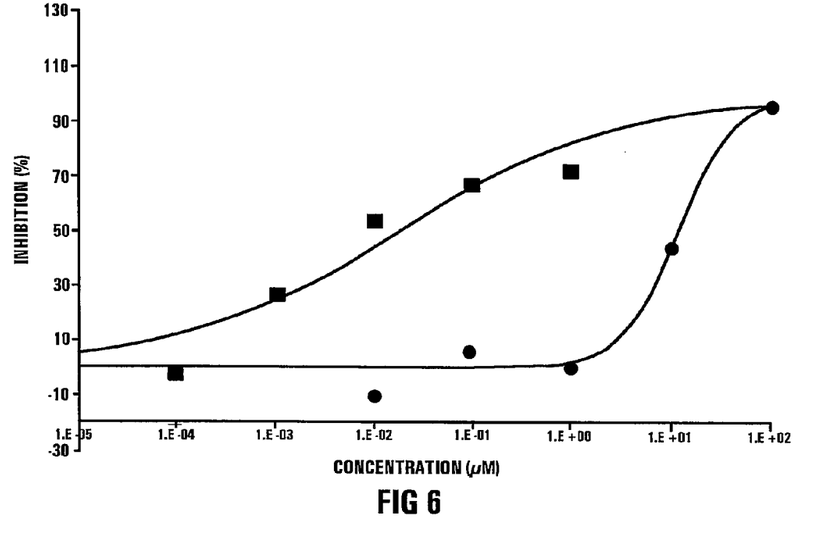
FIG. 6 shows a combined inhibition curve for IL-1 mediator release by both the compound of formula 1, as well as a Dexamethasone standard control.
Figure 7:
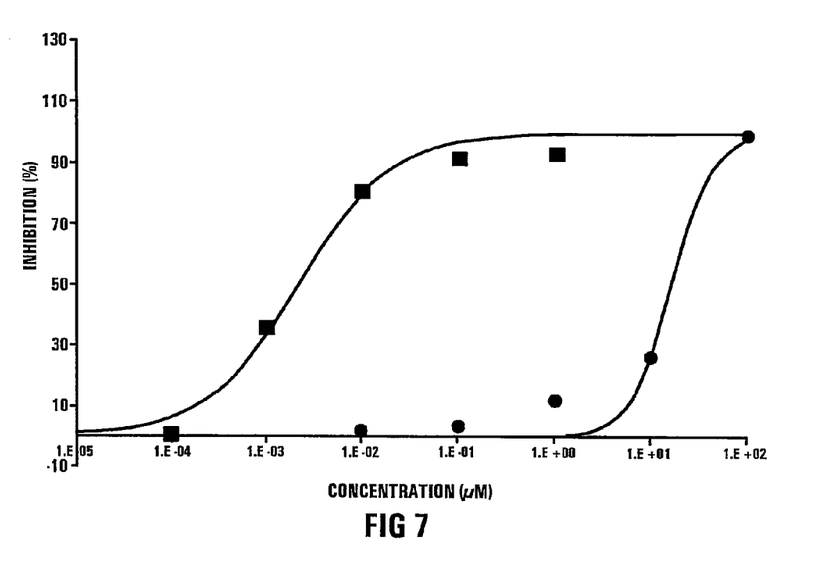
FIG. 7 shows a combined inhibition curve for IL-5 mediator release by both the compound of formula 1, as well as a Dexamethasone standard control, in which the inhibition curve of the compound of formula 1 has been normalised.

Inhibition of the release of Interleukin-5 (IL-5), which is a prominent mediator released in allergic diseases, was also determined for the sesquiterpenoid compound of formula 1 in cellular assays, the inhibition curves of which are shown in FIG. 6 and FIG. 7, respectively. The results obtained for these bio-assays are shown in Table 13 below.

As regards the human IL-5 mediator release text, the test compound is incubated with Concanavalin A (ConA) (10 µg/ml)-stimulated human peripheral blood mononuclear leukocyte (PBMNL) cells in growth medium RPMI-1640 (pH 7.4) overnight at 37° C. in an incubator. The IL-5 cytokine production levels in the conditioned medium are quantified using a sandwich ELISA kit. Compounds are screened at 10, 1, 0.1, 0.01 and 0.001 µM. These same concentrations are concurrently applied to a separate group of treated cells and evaluated for possible compound-induced cytotoxicity only if significant inhibition of release is observed. Dexamethasone is used as standard reference agent.

Figure 2:
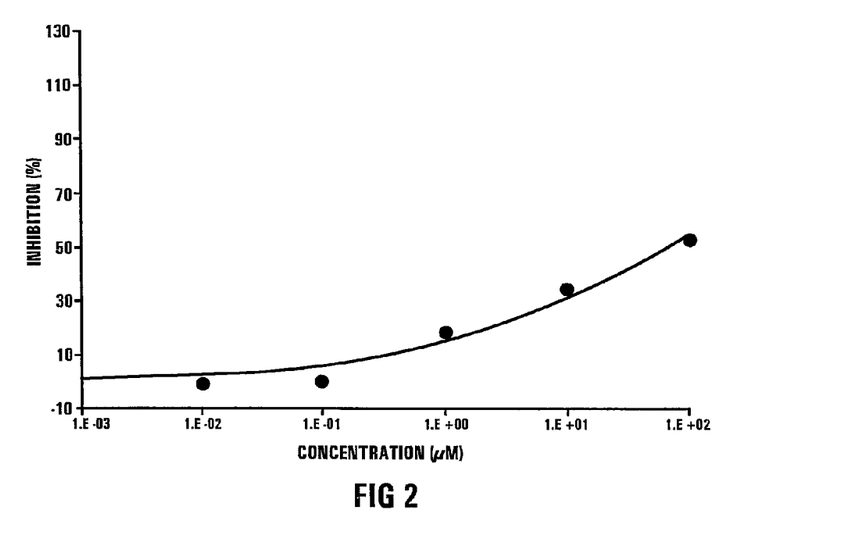
FIG. 2 shows an inhibition curve for Con-A induced cytotoxicity mediator release by the compound of formula 1.

In addition, Con-A cytotoxicity tests were conducted using the compound of formula 1, the inhibition curves of which is shown in FIG. 2.

For the ConA-Induced mediator release/cytotoxicity test, the test compound and/or vehicle is incubated with a suspension of human peripheral blood mononuclear leukocytes (PB-MNL, 1×10$^5$/well) in the presence of Concanavalin A (Con A, 20 µg/ml) in RPMI buffer (pH 7.4) at 37° C. overnight in 5% $CO_2$. AlamarBlue reagent is added and the cells are incubated at 37° C. for 16 hours. Living cells take up AlamarBlue and emit fluorescence. Fluorescence intensity is measured using a SpectraFluor Plus plate reader with excitation at 530 nm and emission at 590 nm. A decrease of 50% or more (50%) in fluorescence intensity relative to the vehicle treated controls indicates significant cytotoxicity. Compounds are screened at 10, 1, 0.1, 0.01 and 0.001 µM. Dexamethasone is used as standard reference agent.

Figure 3:
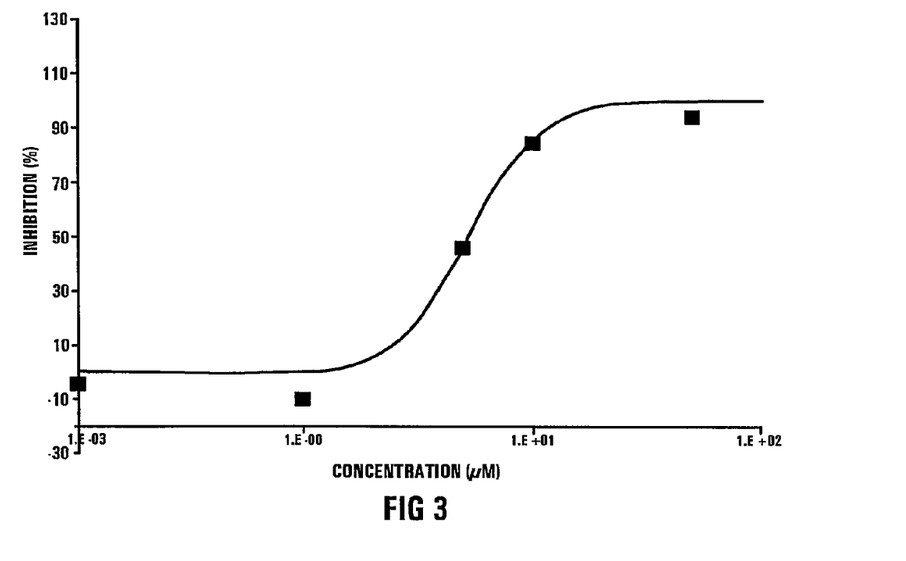
FIG. 3 shows an inhibition curve for Con-A induced cytotoxicity mediator release by a DMSO standard control.
Figure 4:
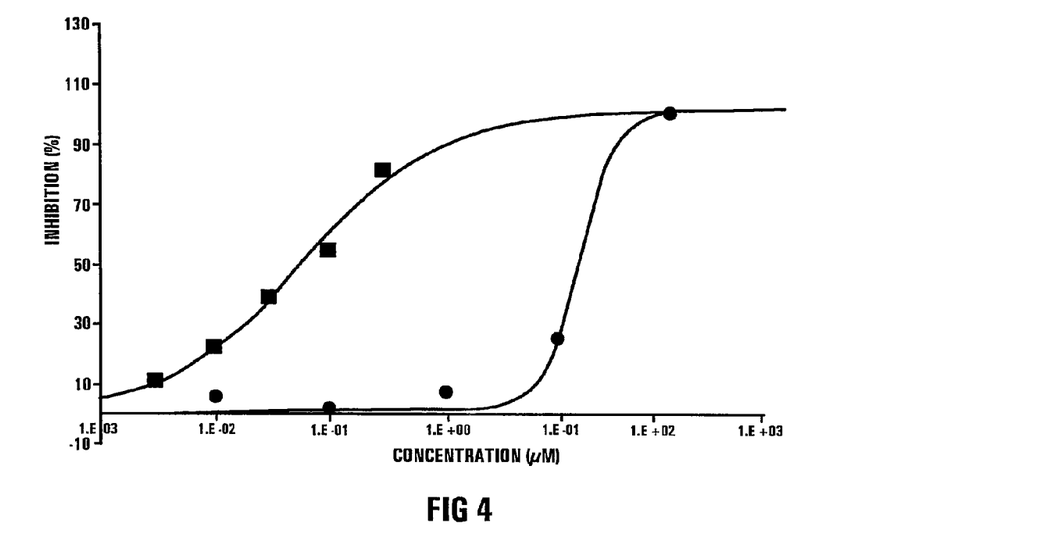
FIG. 4 shows an inhibition or concentration response curve for NF-κB Transcription Response for the compound of formula 1, in which the curve has been normalised.
Figure 5:
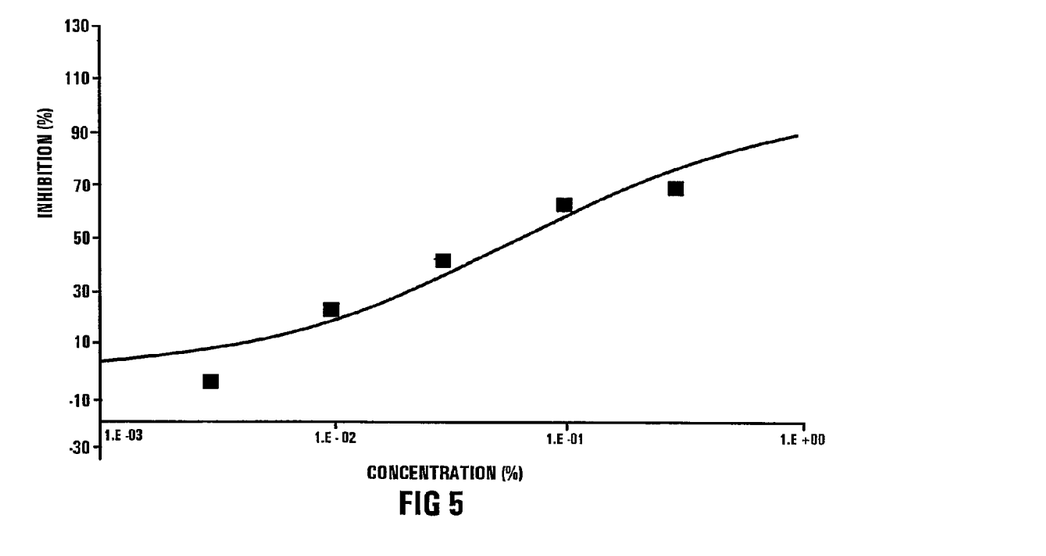
FIG. 5 shows an inhibition cor concentration response curve for NF-κB Transcription Response for a Cyclosporin A positive control.

The results of the control assays (using DMSO) for the above assays is shown in FIG. 3.

TABLE 13

Inhibition of mediator release by sesquiterpenoid compound (1)

| Primary Cellular Assay | Species | Concentration | Criteria | ANT. | $EC_{50}$ |
|---|---|---|---|---|---|
| Mediator Release, IL-5 | hum | 100 µg/ml | ±50% | 93 | 16.1 µM | hum = human; ANT = antagonist

The $IC_{50}$ of the compound is 16.1 µM for the mediator release Interleukin-5 (IL-5) inhibition assay. Inhibition of 93% is observed for the mediator release Interleukin-5 (IL-5) inhibition assay, using 100 µM concentrations of the active compound in each experiment.

Limited cytotoxicity of the active compound was observed when conducting the above bio-assays, as shown in Table 14, see $IC_{50}$ vs $EC_{50}$ values. Although a partial cytotoxic effect was observed during the mediator release assays, the efficacy of the purified compound of formula 1 is ascribed to the fact that effective binding to the glucocorticoid receptor (GR) site was established.

TABLE 14

Cytotoxicity profile of sesquiterpenoid (1)

| Assay | Species | n = | Concentration | Criteria | ANT. | |
|---|---|---|---|---|---|---|
| | | | | | | $IC_{50}$ |
| Cytotoxicity, Mediator Release, Con A-Induced | hum | 2 | 100 µM | ≧±50% | 53 | 58.5 µM |
| | hum | 2 | 10 µM | ≧±50% | 35 | |
| | hum | 2 | 1 µM | ≧±50% | 18 | |
| | hum | 2 | 0.1 µM | ≧±50% | 0 | |
| | hum | 2 | 10 nM | ≧±50% | −1 | |
| | | | | | | $EC_{50}$ |
| Mediator Release, IL-5 | hum | 2 | 100 µM | ≧±50% | 93 | 16.1 µM |
| | hum | 2 | 10 µM | ≧±50% | 36 | |
| | hum | 2 | 1 µM | ≧±50% | 25 | |
| | hum | 2 | 0.1 µM | ≧±50% | 18 | |
| | hum | 2 | 10 nM | ≧±50% | 17 | | hum = human; ANT = antagonist; n = number of tubes

An essential oil, obtained by steam distillation of the dried rhizomes as described in Example 2, was also screened using the 5-lipoxygenase enzyme (5-LO) assay and the phosphodiesterase PDE4 assay to determine the inhibitory effect(s) thereof. Inhibition of 99% was observed using the 5-LO assay, while 73% inhibition was observed using the phosphodiesterase PDE4 assay, indicating that the essential oil has a bronchodilatory effect and may be used to inhibit the action of the 5-lipoxygenase enzyme. The results obtained are also shown in Table 12 above.

Example 5

A diethyl ether extract was prepared in a manner similar to Example 1. The rhizomes of the plant, Siphonochilus aethiopicus, were washed, cut, oven dried at 40° C. and thereafter ground to a powder. 1 l of deionised boiling water was added to 25.0 g of oven dried ground rhizomes and left to stand for 1 hour with occasional stirring. The water was filtered and extracted with diethyl ether (4×500 ml). The ether layers were separated from the water layers, combined, dried ($MgSO_4$), filtered and the solvent removed by means of a rotary evaporator in a water bath at a temperature of 25° C. 215 mg of organic extract was obtained. This diethyl ether extract was submitted for testing.

Chemical fingerprinting of the diethyl ether fraction produced from the aqueous extraction (see experimental procedure above) using LC-MS (combined liquid chromatography-mass spectroscopy) indicated the presence of the major compound, a sesquiterpenoid of formula 1. The diethyl ether extract was purified by flash chromatography (silica gel) using ethyl acetate-hexane (1:9, v/v) as eluent to yield the sesquiterpenoid of formula 1.

Example 6

NF-κB Transcription Biological Assaying

Assays were performed and reference standards used as an integral part of each assay to ensure the validity of the results obtained. The assay is described in Lenardo M J, Baltimaore D. Lenardo M J, Baltimaore D, *NF-κB: A pleiotropic mediator of inducible and tissue specific gene control. Cell.* 58: 227-229, 1989, the contents of which are incorporated herein by way of reference.

Figure 8:
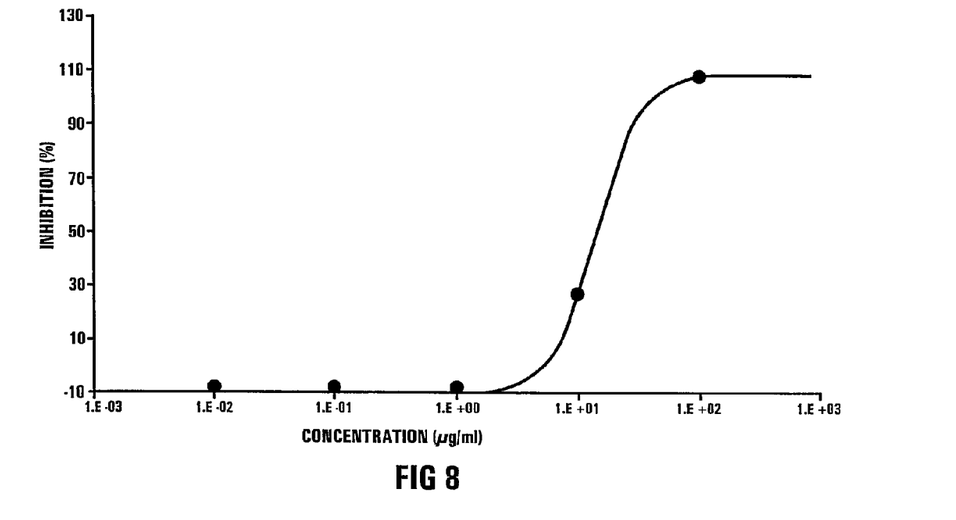
FIG. 8 shows an inhibition or concentration response curve for NF-κB Transcription Response for a diethyl ether extract containing the compound of formula 1, in which the curve has been normalised.
Figure 9:
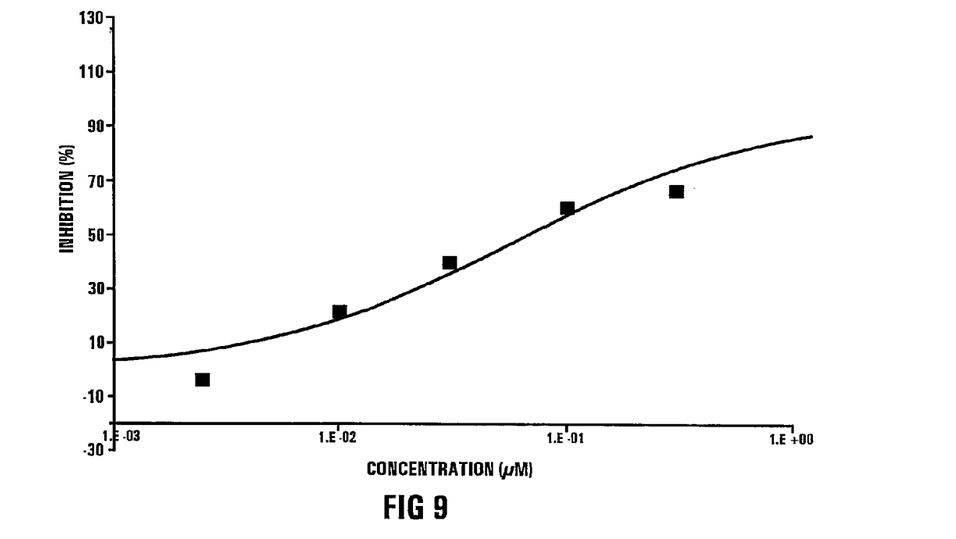
FIG. 9 shows an inhibition or concentration response curve for NF-κB Transcription Response for a Cyclosporin A positive control.

The diethyl ether extract prepared directly from ground plants (FIG. 1) (WG-I-94B) was evaluated for its anti-inflammatory properties in the NF-κB Transcription assay (see protocol below). A significant inhibition activity was observed, with an estimated $IC_{50}$ of 14.3 µg/mL (see Table 15 below) in this assay in the absence of cytotoxicity at concentrations up to 100 µg/mL. Cyclosporin A was used as the reference compound ($IC_{50}$ of 0.0608 µM) (see Table 15 below) in this assay. The inhibition and cytoxicity results are shown in Table 16 and concentration response curves are shown in FIGS. 8 and 9. Based on these results, it was established that the diethyl ether extract was effective in the inhibition of NF-κB.

TABLE 15

Inhibition of NF-κB transcription factor by the ether extract (WG-I-58A)

| Compound | IC50 | NH |
|---|---|---|
| Diethyl ether extract (WG-1-58A) | 14.3 µg/mL | 2.24 |
| Cyolosporin A | 0.0608 µM | 0.751 |

Significant inhibition activity was observed in the NF-κB Transcription Response cellular assay with no cytotoxic effects thereby inhibiting the release of various pro-inflammatory and inflammatory mediators that are responsible for the inflammatory pathway of asthma.

TABLE 16

Cytotoxicity and Inhibition of NF-κB transcription factor by the diethyl ether extract (WG-I-58A), dose response

| Assay | Species | n = | Concentration | Criteria | ANT |
|---|---|---|---|---|---|
| | | | | | $IC_{50}$ |
| Cytotoxicity, Transcription Response NF-κB | hum | 2 | 100 µg/mL | ≧±50% | −4 No Toxicity |
| | hum | 2 | 10 µg/mL | ≧±50% | −2 |
| | hum | 2 | 1 µg/mL | ≧±50% | 0 |
| | hum | 2 | 0.1 µg/mL | ≧±50% | −1 |
| | hum | 2 | 10 µg/mL | ≧±50% | 0 |

TABLE 16-continued

Cytotoxicity and Inhibition of NF-κB transcription factor by the diethyl ether extract (WG-I-58A), dose response

| Assay | Species | n = | Concentration | Criteria | ANT |
|---|---|---|---|---|---|
| | | | | | $EC_{50}$ |
| Transcription Response NF-κB | hum | 2 | 100 µg/mL | ≧±50% | 141 14.3 µg/mL |
| | hum | 2 | 10 µg/mL | ≧±50% | 42 |
| | hum | 2 | 1 µg/mL | ≧±50% | 2 |
| | hum | 2 | 0.1 µg/mL | ≧±50% | 1 |
| | hum | 2 | 10 µg/mL | ≧±50% | 1 | hum = human; ANT = antagonist; n = number of tubes

Example 7

NF-κB Transcription Factor Inhibition by Compound 1

1. Experimental Procedure

The fresh rhizomes and roots of the plant (300 g), *Siphonochilus aethiopicus*, were washed with water and air dried. The freshly roots were separated from the rhizomes. The roots were crushed and the rhizomes were sliced into slices having a thickness of approximately 2-3 mm each. Both the roots and rhizomes were steam stilled in a steam distillation unit for 3 h. The crystals which formed in the condenser were washed out with deionised water and filtered through a sintered glass funnel. The structure of the crystals is given in FIG. 1 (Sample no: WG-I-94B).

The mixture of essential oil and water in the separating funnel condensate was allowed to stand at room temperature for 18 h. The resulting crystals present on the surface, comprising the compound of formula 1 were removed by draining of the condensate and filtering using a sintered glass funnel. A total of 240 mg of the crystals was obtained. The crystals were submitted for testing.

Formula 1

WG-1-94B

2. Biological Assaying

Assays were performed at MDS Pharma in Taiwan and reference standards used as an integral part of each assay to ensure the validity of the results obtained.

The compound of formula 1 was evaluated for its anti-inflammatory properties in the NF-κB cellular transcription response assay (see Attachment I for protocol) as well as the corresponding NF-κB cellular transcription response cytotoxicity assay. The compound caused >100% inhibition at 100 µM in the NF-κB cellular transcription response assay, with no apparent cytotoxicity at the same concentration. This shows that compound inhibition in the NF-κB cellular transcription is not due to general cytotoxicity. An $IC_{50}$ of 15.6 µg/mL was calculated in this assay and Cyclosporin A was used as the reference compound ($IC_{50}$ of 0.0608 µM). The results and concentration response curves are shown in Attachment II. Based on these results, it was established that the compound of formula 1 was effective in the inhibition of NF-κB.

3. Beneficial Properties

The compound, a sesquiterpenoid, isolated from *Siphonochilus aethiopicus* was evaluated in in vitro assays that play a central role in chronic inflammatory diseases, such as asthma. Significant inhibition activity was observed in the NF-κB cellular transcription response assay with no cytotoxic effects. The compound (isolated from steam distillation of the freshly prepared roots and rhizomes) can thus be used to inhibit specific activity of the NF-κB transcription response, thereby inhibiting the release of various pro-inflammatory and inflammatory mediators that are responsible for the inflammatory pathway of asthma. NF-κB represents a master regulator of inflammation and is, therefore, an attractive target for drug development.

Example 8

Transcription Response, NF-κB (Human)

Test Number: 361000

Introduction:

In resting cells, cytoplasmic location of the nuclear transcription factor NF-κB is bound by an inhibitory subunit IκB; binding of IκB effectively masks the nuclear localization sequences present on the P50 and P65 subunits of NF-κB, preventing nuclear translocation. It appears that upon cellular stimulation, a signal transduction pathway is activated leading to phosphorylation of key serine residues in the IκB polypeptide whereupon the NF-κB-IκB complex dissociates, IκB is rapidly degraded, and the unmasked nuclear localization signal allows NF-κB to translocate into nuclei and activate the transcription of specific genes. It is known that NF-κB regulates many pro-inflammatory and pro-thrombic factors produced by activated leukocytes. NF-κB represents a master regulator of inflammation and is, therefore, an attractive target for drug development.

Procedure:

Human T lymphocytic Jurkat cells, transfected with a response element-lacZ reporter in which transcription of the β-galactosidase gene is directed by the binding site for the NF-κB transcription factor, are used. Test compound and/or vehicle are incubated with the cells ($1.5 \times 10^6$/ml) in the presence of 0.5 μM A23187 and 50 ng/ml PMA (phorbol 12-myristate 13-acetate) in RPMI-1640 pH 7.4 at 37° C. for 4 hours. Test compound-induced β-galactosidase activity is determined by the conversion of FDG (fluorescein di-β-D-galactopyranoside) to fluorescein. Fluorescence intensity is read on SpectroFluor Plus plate reader. Decrease of 50 percent or more (50%) in fluorescence intensity, relative to 10 μM cyclosporin A, indicates significant inhibitory activity. Compounds are screened at 10, 1, 0.1, 0.01 and 0.001 μM. These same concentrations are concurrently applied to a separate group of treated cells and evaluated for possible compound-induced cytotoxicity only if significant stimulation or inhibition is observed (Cat. #361100).

| Reference Data: | |
| --- | --- |
| Inhibitor | $IC_{50}$ (nM) |
| *Cyclosporin A | 50 |

*Indicates standard reference agent used.

TABLE 17

Assay results - Cytotoxicity and efficacy (transcription response) results for compound 1 (WG-I-94B)
EXPERIMENTAL RESULTS - FUNCTIONAL ASSAYS
CELLULAR ASSAYS

| | | Tissue, | | | | | % RESPONSE | | | |
| --- | --- | --- | --- | --- | --- | --- | --- | --- | --- | --- |
| Cat. # | Assay Name | Batch* | Species | n= | Conc. | Criteria | Resp | AG | Ant | R |
| 361100 | Cytotoxicity, Transcription Response NF-κB | 161790 | hum | 2 | 100 μM | ≧±50% | | | −3 | |
| | | 161790 | hum | 2 | 10 μM | ≧±50% | | | 2 | |
| | | 161790 | hum | 2 | 1 μM | ≧±50% | | | 2 | |
| | | 161790 | hum | 2 | 0.1 μM | ≧±50% | | | 6 | |
| | | 161790 | hum | 2 | 10 μM | ≧±50% | | | 1 | |
| ◆361000 | Transcription Response, NF-κB | 161012 | hum | 2 | 100 μM | ≧±50% | | | 113 | |
| | | 161012 | hum | 2 | 10 μM | ≧±50% | | | 27 | |
| | | 161012 | hum | 2 | 1 μM | ≧±50% | | | 7 | |
| | | 161012 | hum | 2 | 0.1 μM | ≧±50% | | | 0 | |
| | | 161012 | hum | 2 | 10 μM | ≧±50% | | | 5 | |

*Batch: Represents compounds tested concurrently in the same assay(s)‡ Partially soluble in in vitro test solvent
◆Denotes item meeting criteria for significance
Ag = Agonist; ant. = Antagonist; Resp. = Response; ND = Assay Test Not Done; R = Additional Comments
hum = human

Example 9

Effect of Ether Extraction in In Vivo Asthmatic Rat Models

Background

Many cytokines exist that are known mediators of inflammation and are involved in the asthmatic disease process. When a causative agent like an allergen is inhaled, the bronchial epithelial cells are activated and produce certain pro-inflammatory cytokines (interleukins, abbreviated IL) in particular the chemokine IL-8.

From the outcome of previous in vitro assays, a suitable in vivo animal model was selected to determine the anti-asthmatic and anti-allergic activity of the diethyl ether extract (WG-I-101) of the plant, *Siphonochilus aethiopicus*.

Experimental Procedure

The rhizomes of the plant, *Siphonochilus aethiopicus*, were washed, cut, oven dried at 40° C. and thereafter ground to a powder. 5 L of diethyl ether was added to 110.40 g of oven dried ground rhizomes and left to stand for 1 hour with occasional stirring. The diethyl ether was filtered and extracted with diethyl ether (4×2 L). The ether layers were combined, dried ($MgSO_4$), filtered and the solvent removed by means of a rotary evaporator in a water bath at a temperature of 25° C. 1.075 g of organic extract was obtained. This diethyl extract (sample no: WG-I-101) was submitted for testing.

Biological Assaying

Assays were performed at MDS Pharma in Taiwan and reference standards used as an integral part of each assay to ensure the validity of the results obtained. The biological assay employed was the Pulmonary, Antigen/Lipoxygenase Metabolites assay and the diethyl ether extract of *Siphonochilus aethiopicus* was evaluated for possible activity in this in vivo assay.

(1) Test Substance and Dosing Pattern

WG-I-101 was suspended in 0.5% CMC/0.1% Tween 80. The test substance at a dose of 500 mg/kg was given orally twice daily for 3 consecutive days and an additional final dose was added at one hour before challenge of Ovalbumin on testing day. Dosing volume of 10 ml/kg was used. The formulation is summarized as follows:

| Test Compound | Vehicle | Solubility[a] | Colour | Light Protection[b] | Temperature[c] | Formula mg/ml |
|---|---|---|---|---|---|---|
| WG-I-101 | 0.5% CMC/0.1% Tween 80 | I | Brown | Y | RT | 50 |

[a]This is based upon visual observation
S: soluble; I: Insoluble
ppt: precipitation
[b]Y: formula is kept in tube or vial with brown colour, or covered with aluminium foil
[c]TR: room temperature; prepared and stored under 15° C.~30° C. Temperature throughout experiment, lower or higher than room temperature is specified.

(2) Animals

Male Dunkin-Hartley derived guinea pigs provided by Laboratory Animal Center of National Taiwan University College of Medicine were used. Space allocation for animals was as follows: 45×23×21 cm for 3 guinea pigs. Each animal cage was sterilized with autoclave. All animals were maintained in a controlled temperature (22°-24° C.) and humidity (60%-80%) environment with 12 hour/light dark cycles for at least one week in the laboratory prior to use. Free access to standard lab chow (PMI Nutrition International, Inc., USA) and RO water was granted. All aspects of this work including housing, experimentation and disposal of animals were performed in general accordance with the Guide for the Care and Use of Laboratory Animals (National Academy Press, Washington, D.C., 1996).

(3) Method

Groups of 5 Dunkin-Hartley derived male guinea pigs weighing 400±50 g (final day) were employed. The animals were anesthetized with pentobarbital sodium (50 mg/kg IP, with an additional 15 mg/kg IP if needed). An aluminum plate kept at 37° C. through water flow from a bath was placed beneath the test animals to maintain body temperature. The trachea was cannulated and a rodent ventilator (Harvard, USA) was used for artificial ventilation (10 ml/kg, 50 breaths/minute). Through a side-arm of the cannula, intratracheal pressure (ITP) was measured using a Pneumatic pulse transducer (Narco Biosystem, USA). A carotid artery was cannulated (PE50, Clay Adams, USA) for measurements of blood pressure using a Stathem P23×L transducer (Viggo-Spectramed, USA) and heart rate was obtained from lead II ECG. Guinea pigs were sensitized with IP injections of ovalbumin (0.5 µg/0.5 ml/animal) and Al $(OH)_3$ (1 mg/0.5 ml/animal) on days 1 and 8. The animals were then challenged with 15 µg/kg of Ovalbumin (IV) between days 19 and 23 and bronchopulmonary constriction was recorded as an increase in ITP.

The test substance at 500 mg/kg was administered orally twice daily for 3 consecutive days and an additional final dose was added on testing day, then, one hour after final dose, the animals were injected intravenously (1 ml/kg) with a "cocktail": Indomethacin (10 mg/kg), Mepyramine (2 mg/kg), and Propranolol (100 µg/kg), followed by challenge with ovalbumin 5 minutes later. In vehicle-treated animals, antigen challenge resulted in bronchoconstrictor responses (increase in ITP) ranging from 45 to 85 percent of maximum possible bronchoconstriction as measured by complete tracheal occlusion. A 50 percent or more ($\geq 50\%$) inhibition of the ovalbumin-induced bronchoconstriction relative to the vehicle-treated control animals is considered significant. Bronchoalveolar lavage fluid was retrieved after instilling 5 ml of phosphate buffered saline for 2 times. TNF-α, IL-1β and IL-8 in bronchoalveolar lavage fluid (BALF) supernatants were measured with ELISA after ovalbumin challenge. One-way ANOVA followed by Dunnett's Test was applied for comparison between the vehicle control and test compound-treated groups. P<0.05 is considered significant.

(4) In Vivo Assay Results

The results of the assay is summarised in Table 18 and showed that the diethyl ether extract (WG-I-101) caused moderate inhibition (19%) of the Ovalbumin-induced acute airway constriction relative to the vehicle-treated control (Table 18). ($\geq 50\%$) inhibition is regarded as significant)

TABLE 18

Guinea pig in vivo assay results
Assay # 570000 Pulmonary, Antigen/Lipoxygenase Metabolites, in Guinea Pigs
Intratracheal Pressure (ITP)

| Treatment | Route | Dose | N | ΔITP[1] (cm H$_2$O) (−) Oval | ΔITP[1] (cm H$_2$O) (+) Oval | % Control[2] | % Inhibition[3] |
|---|---|---|---|---|---|---|---|
| Vehicle | PO | 10 ml/kg | 1 | 0 | 25.2 | | |
| (0.5% CMC/ | | bidx 3 & qdx1 | 2 | 0 | 9.6 | | |
| 0.1% Tween 80) | | | 3 | 0 | 9.0 | | |
| | | | 4 | 0 | 10.2 | | |
| | | | 5 | 0 | 25.2 | | |
| | | | X ± SEM | 0 | 15.8 ± 3.8 | 0 | — |
| PT# 1083892 | PO | 500 mg/kg | 1 | 0 | 6.6 | | |
| (CIR-235) (WG-1- | | bidx 3 & qdx1 | 2 | 0 | 12.0 | | |
| 101) (crude diethyl | | | 3 | 0 | 16.8 | | |
| ether plant extract) | | | 4 | 0 | 15.6 | | |
| | | | 5 | 0 | 13.2 | | |
| | | | X ± SEM | 0 | 12.8 ± 1.8 | 0 | 19 |
| Phenidone | IV | 30 mg/kg | 1 | 0 | 4.8 | | |
| | | qdx1 | 2 | 0 | 1.8 | | |
| | | | 3 | 0 | 1.2 | | |
| | | | 4 | 0 | 0.6 | | |
| | | | 5 | 0 | 0.6 | | |
| | | | X ± SEM | 0 | 1.8 ± 0.8 | 0 | (89) |

Anesthetized and artificially ventilated guinea pigs previously sensitized were pretreated with Mepyramine 2 mg/kg, Indomethacin 10 mg/kg and Propranol 0.1 mg/kg for 5 minutes; arterial blood pressure (BP, mm Hg), heart rate (HR, beats/min.) and tracheal pressure (TP, cm H2O) were recorded after oral dosing for 3 days. At the end of chronic dosing, antigen (Ovalbumin 15 μg/kg IV)-induced increase in tracheal pressure (ITP) above an initial baseline of 6 cm H2O was then recorded as an indication of bronchoconstriction. Percent (%) inhibition is calculated according to the formula of [Increase in Tracheal Pressure (vehicle-treated)]−[Increase in Tracheal Pressure (test substance-treated)/[Increase in Tracheal Pressure (vehicle-treated)]×100%.

1. ΔITP: Changes in ITP over corresponding baseline values; (−) Oval: Response to vehicle or test substance alone and before Ovalbumin challenge; (+) Oval: Changes in response to Ovalbumin challenge.
2. % Control: ITP response to test substance, vehicle expressed in terms of percentage of the ITP response to Ovalbumin (15 μg/kg IV) in the vehicle-treated control (100%).
3. A 50 percent or greater (≧50%) inhibition of the Ovalbumin-induced bronchoconstriction relative to the vehicle-treated control is considered significant.

Bronchoalveolar lavage fluid (BALF) samples in the WG-I-101-treated group were prepared for measurements of TNF-α, IL-1β and IL-8 after ovalbumin challenge. One-way ANOVA followed by Dunnett's test was applied for comparison between the vehicle control and test compound-treated groups. P<0.05 is considered significant. WG-I-101 caused great inhibition of IL-8 production (P<0.05) versus control after ovalbumin challenge in guinea pigs, without significant effects on TNF-α and IL-1β secretion. Results are shown in Table 19.

TABLE 19

Cytokine expression results

| Treatment | Route | Dose | N | TNF-α (pg/ml) | IL-1β (pg/ml) | IL-8 Cont(pg/ml) | BAL Retrieved Volume (ml) |
|---|---|---|---|---|---|---|---|
| Vehicle | PO | 10 ml/kg | 1 | 1.44 | 2.07 | 0.25 | 4.5 |
| (0.5% CMC/ | | bidx 3 | 2 | 12.94 | 2.06 | 26.87 | 7.2 |
| 0.1% Tween 80) | | qdx1 | 3 | 10.97 | 0.42 | 28.53 | 5.0 |
| | | | 4 | 11.93 | 4.39 | 29.89 | 6.2 |
| | | | 5 | 3.07 | 2.42 | 3.85 | 4.5 |
| | | | X | 8.07 | 2.27 | 17.88 | 5.5 |
| | | | SEM | 2.41 | 0.63 | 6.51 | 0.5 |
| PT# 1083892 | PO | 500 mg/kg | 1 | 7.43 | 2.08 | 0.00 | 6.4 |
| (CIR-235) | | bidx3 | 2 | 18.42 | 0.71 | 0.00 | 7.2 |
| (WG-1-101) | | qdx1 | 3 | 12.43 | 4.22 | 0.00 | 7.3 |
| | | | 4 | 13.44 | 1.85 | 0.00 | 7.3 |
| | | | 5 | 9.68 | 0.23 | 0.00 | 7.3 |
| | | | X | 12.28 | 1.82 | 0.00* | 7.1 |
| | | | SEM | 1.86 | 0.69 | | 0.2 |
| Phenidone | IV | 30 mg/kg | 1 | 12.03 | 3.10 | 3.63 | 7.8 |
| | | qdx1 | 2 | 7.0 | 0.24 | 1.22 | 7.5 |
| | | | 3 | 3.79 | 0.46 | 0.00 | 7.5 |
| | | | 4 | 8.96 | 2.25 | 0.00 | 8.2 |
| | | | 5 | 6.33 | 0.00 | 0.00 | 7.8 |

TABLE 19-continued

Cytokine expression results

| Treatment | Route | Dose | N | TNF-α (pg/ml) | IL-1β (pg/ml) | IL-8 Cont(pg/ml) | BAL Retrieved Volume (ml) |
|---|---|---|---|---|---|---|---|
| | | | X | 7.62 | 1.21 | 0.97* | 7.8 |
| | | | SEM | 1.38 | 0.62 | 0.71 | 0.1 |

Bronchoalveolar lavage fluid (BALF) samples in the WG-I-101 treated group were prepared for measurements of TNF-α, IL-1β and IL-8 after Ovalbumin challenge. TNF-α, IL-1β and IL-8 levels of each sample were assessed using TNF-α, IL-1β and IL-8 ELISA kits, respectively. One way ANOVA followed by Dunnett's Test was applied for comparison between the vehicle control and test compound-treated groups. P<0.05 is considered significant.

Example 10

Pulmonary, Antigen/Lipoxygenase Metabolites

Test Number: 570000
Procedure:

Groups of 5 male Dunkin-Hartley guinea pigs weighing 250±50 g are anesthetized with pentobarbital sodium (50 mg/kg i.p., plus an additional 15 mg/kg i.p. if required) and succinylcholine chloride (2 mg/animal i.p.) is subsequently administered to prevent spontaneous respiration. Body temperature is maintained at 37° to 38° C.

The trachea is cannulated and the guinea pig ventilated with a Harvard rodent respirator in a closed system. Tracheal pressure is recorded through a side-arm of the cannula connected to a P23ID Statham transducer. Respiratory rate set at 50 strokes/minute with a stroke volume (approximately 1 ml/100 g) sufficient to produce a baseline tracheal pressure of 6 cm $H_2O$. Mean arterial pressure is monitored from a cannulated carotid artery, and heart rate is obtained from chest electrodes arranged for lead II. The jugular vein is cannulated for i.v. vehicle or drug administration in a volume of 1 ml/kg.

Lipoxygenase is activated and resultant leukotrienes generated through antigen challenge in previously sensitized animals. Guinea pigs are sensitized with injections of ovalbumin and $Al(OH)_3$ (0.5 µg and 1 mg, respectively in a volume of 0.5 ml/animal i.p.) on day 1, boosted with the same dose of ovalbumin and $Al(OH)_3$ on day 8, and challenged between day 19 and 23 with ovalbumin (50 µg/kg i.v.) to effect a maximal-induced airway constriction, reflected as an increase in tracheal pressure (cm $H_2O$). Also, an increase in tracheal pressure could be related to an increase in stiffness of the respiratory system. The animals are pretreated with CSIR compound by oral gavage for two days. On the day of experiment, the animals are administered with CSIR compound 30 min before anesthesia and surgery which takes 15 min. The ovalbumin challenge is administered 60 min after dosing with CSIR. The animals are pretreated 5 minutes before test substance administration with i.v. indomethacin (10 mg/kg), mepyramine (2 mg/kg), and propranolol (0.1 mg/kg): a "cocktail" designed to inhibit the generation of cyclooxygenase products (thromboxanes, etc.) as well as antagonize histamine and β-adrenergic receptors. In vehicle-treated control animals, antigen challenge results in airway constrictor responses ranging form 45 to 85 percent of maximum possible airway constriction obtained by tracheal occlusion.

Phenidone, the positive standard, is administered i.v. (30 mg/kg) 5 minutes before ovalbumin challenge in 5 guinea pigs. A 50 percent or more ($\geqq 50$) inhibition of the induced airway constriction relative to vehicle treated control animals is considered significant.

| Reference Data: | |
|---|---|
| Compound | MED mg/kg i.v. |
| Atropine | >10 |
| Cromolyn Sodium | >100 |
| LY-171883 | 30 |
| NDGA | 10 |
| Phenidone* | 30 |
| Salbutamol | 0.1 |
| Theophylline | 50 |

*standard reference agent used
LY-171883 = 1[2-hyroxy-3-propyl-4-[4-(1H-tetrazol-5-yl)butoxy]phenyl]ethanone;
NDGA = nordihydroguaretic acid Note:

Test substances active in this model system indicate possible in vivo inhibition of lipoxygenase activity and/or antagonism of its leukotriene(s) generated receptor activation. Consequently, it may be worthwhile to compare results in this model system with those obtained from: cyclooxygenase inhibition to determine specificity for enzyme inhibition; leukotriene $D_4$ antagonism to determine test substance action on enzyme end-product receptor activation relative to lipoxygenase enzyme inhibition; and anticholinergic activity and/or antihistamine $H_1$ and $H_3$ activity to determine selectivity for receptor antagonism and/or bronchodilator action.

TABLE 20

IUPAC names of compounds referred to in Table 1 above.

| Common name | IUPAC Name |
|---|---|
| Alpha-pinene | 2,6,6-Trimethylbicyclo (3.1.1) hept-3-ene |
| Sabinene | 4-Methylene-1-(1-methylethyl) bicyclo (3.1.0) hexane |
| Myrcene | 7-Methyl-3-methylene-1,6-octadiene |
| Delta-3-carene | 3,7,7-Trimethylbicyclo (4.1.0) hept-3-ene |
| Alpha - terpinene | 1-Methyl-4-(1-methylethyl)-1,3-cyclohexadiene |
| Beta-phellandrene | 3-Methyl-6-(1-methylethyl) cyclohexene |
| Cis-ocimene | 3,7-Dimethyl-(Z)-octatriene |
| Trans-beta-ocimene | 3,7-(E)-dimethyloctatriene |
| Gamma- terpinene | 1-Methyl-4-(1-methylethyl)-1,4-cyclohexadiene |
| Allo - neo - ocimene | 2,6-Dimethyl-(E,E)-2,4,6-octatriene |
| Allo - ocimene | 2,6-Dimethyl-(E,Z)-2,4,6-octatriene |
| Beta - elemene | 1-Ethenyl-1-methyl-2,4-bis (1-methylethenyl)-(1S-(1-alpha,2-beta,4-beta))-cyclohexane |
| Germacrene - D | 1-Methyl-5 methylene-8-(1-methylethyl)-(S-(E,E))-1,6-cyclodecadiene |
| Kessane | Octahydro-1,3,3,6-tetramethyl-(1S-(1-alpha, 4-alpha, 5a-beta, 6-alpha, 8a-alpha))-1,4-ethano-1H-cyclopent(c) oxepin |
| Germacrene - B | 1,5-Dimethyl-8-(1-methyl ethylidene)-(E,E)-1,5-cyclodecadiene |

The extracts of the invention are non-steroidal components isolated in a natural form, but having the same mode of action as steroidal compounds commonly used for the preventative treatment of allergic disease, such as asthma and atopy.

In addition, the sesquiterpenoid compound of formula 1 of the invention shows activity as a leukotriene modifier, inhibiting the actions of inflammatory mediators and leukotrienes.

When used in the form of an essential oil, the extract has a combined effect, in that reduction of asthma and allergy inflammation occurs through bronchodilation, inhibition of leukotriene biosynthesis, as well as due to downregulation of glucocorticoid receptors.

Further, a diethyl ether extract containing the sesquiterpenoid compound of formula 1 of the invention shows significant inhibition activity in the NF-KB Transcription Response cellular assay with no cytotoxic effects. The diethyl ether extract can thus be used to inhibit specific activity of the NF-κB Transcription Response, thereby inhibiting the release of various pro-inflammatory and inflammatory mediators such as the cytokine Interleukin-8 (IL-8) that are responsible for the inflammatory pathway of asthma.

Further, a diethyl ether extract containing the sesquiterpenoid compound of formula 1 of the invention shows significant inhibition in the production of IL-8 an inflammatory cytokine responsible for the inflammatory pathway of asthma.

The invention may be effective in the overall preventative treatment and remission of allergic diseases such as asthma, adding a useful tool in the management of these diseases.

Remission of allergic diseases and asthma is specifically defined for the purposes of this specification as a symptom-free period without subjects taking conventionally available treatment. This remission period is longer than the period that is obtained using conventional treatment for the management of allergic diseases such as asthma.

The Applicant further believes that the invention, in the form of organic solvent extracts, dried rhizomes, an essential oil, or as the single chemical compound of formula 1, either used alone or in combination, or as compositions, provides an alternative to the use of steroidal anti-inflammatory drugs such as glucocorticoids for the long-term preventative treatment and remission of allergic diseases, especially asthma and atopy.

Commercially available agents known to the Applicant which operate at the glucocorticoid receptor level typically are of a steroidal nature and have numerous detrimental side effects during long-term use thereof. The compounds, derivatives, compositions and products of the invention are non-steroidal in nature, yet, surprisingly, have been found to act efficiently at the glucocorticoid receptor (GR) level.

While various embodiments of the present invention have been described in detail, it will be apparent that further modifications and adaptations of the invention will occur to those skilled in the art. It is to be expressly understood that such modifications and adaptations are within the spirit and scope of the present invention.

The invention claimed is:

1. A method for the treatment of asthma or atopy, consisting essentially of administering to a subject in need thereof a therapeutically effective amount of a medicament of an extract of the plant species *Siphonochilus aethiopicus*, the extract including, as an active ingredient, a compound selected from the group consisting of a compound having the structural formula 1, (4a-S, 5R, 8a-R or 4a-R, 5S, 8a-S)

stereoisomers thereof and mixtures thereof.

2. The method as claimed in claim 1, in which the extract is an essential oil obtained by steam distillation of plant material from the plant.

3. The method as claimed in claim 1, wherein the extract is an organic solvent extract obtained by extraction of plant material of the plant with an organic solvent.

4. The method as claimed in claim 3, wherein the organic solvent is an ether selected from the group consisting of diethyl ether, diisopropyl ether, t-butyl methyl ether, t-amyl methyl ether and t-butyl ethyl ether.

5. The method as claimed in claim 3, wherein the organic solvent is an ester selected from the group consisting of methyl acetate, ethyl acetate and benzyl acetate.

6. The method as claimed in claim 2, wherein the plant material is obtained from roots or rhizomes of the plant.

* * * * *